United States Patent [19]
Mendolia et al.

[11] Patent Number: 5,874,069
[45] Date of Patent: Feb. 23, 1999

[54] COSMETIC COMPOSITION CONTAINING SILICON-MODIFIED AMIDES AS THICKENING AGENTS AND METHOD OF FORMING SAME

[75] Inventors: Michael S. Mendolia, Bridgewater; Paul J. Vincenti, Jefferson, both of N.J.; Yigal Blum, San Jose, Calif.; Huiyong (Paul) Chen, Sunnyvale, Calif.; Hui-Jung Wu, Fremont, Calif.

[73] Assignee: Colgate-Palmolive Company, New York, N.Y.

[21] Appl. No.: 790,349

[22] Filed: Jan. 24, 1997

[51] Int. Cl.$^6$ ..................................... A61K 7/32
[52] U.S. Cl. ................ 424/65; 424/66; 424/67; 424/68; 424/401; 514/63
[58] Field of Search ............... 424/401, 65, 66, 424/67, 68, 78.08; 514/63

[56] References Cited

U.S. PATENT DOCUMENTS

| | | | |
|---|---|---|---|
| 2,900,306 | 8/1959 | Slater | 424/65 |
| 3,148,125 | 9/1964 | Strianse et al. | 424/65 |
| 3,255,082 | 6/1966 | Barton | 424/68 |
| 3,288,754 | 11/1966 | Green | 528/26 |
| 3,341,501 | 9/1967 | Hedrick et al. | 528/320 |
| 3,457,323 | 7/1969 | Stengle | 525/431 |
| 3,637,550 | 1/1972 | Sprauer | 525/420 |
| 3,903,046 | 9/1975 | Greber et al. | 525/431 |
| 3,948,835 | 4/1976 | Greber et al. | 525/431 |
| 4,049,792 | 9/1977 | Elsnau | 424/66 |
| 4,137,306 | 1/1979 | Rubino et al. | 424/68 |
| 4,279,658 | 7/1981 | Harvey et al. | 106/217.2 |
| 4,322,400 | 3/1982 | Yuhas | 424/59 |
| 4,346,079 | 8/1982 | Roehl | 424/65 |
| 4,429,082 | 1/1984 | Lee et al. | 525/426 |
| 4,647,630 | 3/1987 | Schmid et al. | 525/431 |
| 4,675,374 | 6/1987 | Policastro et al. | 525/474 |
| 4,783,511 | 11/1988 | Schmid | 525/431 |
| 4,806,338 | 2/1989 | Smith | 424/47 |
| 4,853,214 | 8/1989 | Orr | 424/69 |
| 4,937,069 | 6/1990 | Shin | 424/66 |
| 5,013,577 | 5/1991 | Wright et al. | 427/503 |
| 5,069,897 | 12/1991 | Orr | 424/66 |
| 5,102,656 | 4/1992 | Kasat | 424/66 |
| 5,164,522 | 11/1992 | McCarthy et al. | 554/39 |
| 5,196,499 | 3/1993 | O'Lenick, Jr. | 528/15 |
| 5,210,133 | 5/1993 | O'Lenick, Jr. | 525/54.1 |
| 5,243,010 | 9/1993 | Choi et al. | 528/28 |
| 5,272,241 | 12/1993 | Lucarelli et al. | 528/15 |
| 5,302,381 | 4/1994 | Greczyn et al. | 424/66 |
| 5,500,209 | 3/1996 | Ross et al. | 424/66 |
| 5,603,925 | 2/1997 | Ross et al. | 424/65 |
| 5,632,974 | 5/1997 | Galleguillos et al. | 424/66 |

FOREIGN PATENT DOCUMENTS

| | | |
|---|---|---|
| 291334 A2 | 11/1988 | European Pat. Off. |
| 2299024 | 9/1996 | United Kingdom . |
| 9524887 | 9/1995 | WIPO . |
| 9615761 | 5/1996 | WIPO . |
| WO 96/27364 | 9/1996 | WIPO . |
| WO 96/32927 | 10/1996 | WIPO . |

*Primary Examiner*—Jose' G. Dees
*Assistant Examiner*—Michael A. Williamson
*Attorney, Agent, or Firm*—Rosemary M. Miano; William I. Solomon

[57] ABSTRACT

A base composition and corresponding cosmetic composition are disclosed which can be formed as solids (for example, gels or sticks) and which comprise a solvent which includes a silicone fluid (for example, a silicone oil such as cyclomethicone) and a thickening agent formed from a wax and a polyamide gellant wherein at least one of the wax and polyamide includes silicon-containing moieties (for example, siloxane groups to have a siloxane diamide wax to enhance compatibility of the silicone fluid in the composition. A cosmetically active material, such as a deodorant or antiperspirant active material, is included in the composition to form a solid cosmetic product (antiperspirant or deodorant product), which can be a clear product. Compositions of the present invention can be made with increased amounts of silicone fluid and with improved aesthetics such as decreased tack.

49 Claims, No Drawings

COSMETIC COMPOSITION CONTAINING SILICON-MODIFIED AMIDES AS THICKENING AGENTS AND METHOD OF FORMING SAME

BACKGROUND OF THE INVENTION

The present invention is directed to a base composition and cosmetic compositions made therefrom wherein the base composition comprises a (1) silicone fluid and (2) a gelling agent comprising a wax containing siloxane units and a polyamide wherein the polyamide may itself optionally contain siloxane units. The cosmetic compositions include, but not limited to, a deodorant or antiperspirant composition, in solid (for example, gel or stick) form, having a cosmetically active ingredient (illustratively, a deodorant and/or antiperspirant active material) therein. In particular, the present invention is directed to a deodorant or antiperspirant stick or gel composition, utilizing a polyamide gelling agent, having enhanced compatibility with silicone fluids (for example, silicone liquids, such as silicone oils). The cosmetic composition of the present invention, when incorporating an antiperspirant and/or deodorant active material, can be used to combat body malodor, for example, in axillary regions of the human body, by applying the composition to the human body (for example, to the skin, in axillary regions of the body).

The present invention is particularly directed to clear or transparent antiperspirant compositions in stick or gel form. More particularly, the present invention is directed to a clear gel or stick composition including a polyamide gelling agent, and having an active ingredient (for example, an antiperspirant active material) incorporated therein, the composition having improved application and cosmetic properties (including reduced tackiness and stickiness). The present base compositions and cosmetic compositions are preferably transparent (clear) but they can also be translucent or opaque.

Antiperspirant products are well known in the art. Antiperspirant products have appeared in the marketplace in various dosage forms, such as sticks, gels, roll-ons, aerosols and creams. Generally, these dosage forms include a solution of the active ingredient in a suitable solvent, a suspension of the active ingredient in a non-solvent, or a multiphasic dispersion or emulsion in which a solution of the active ingredient is dispersed in some continuous phase or in which the solubilized active ingredient constitutes the continuous phase.

With respect to solid cosmetic compositions, the stick form can be distinguished from a gel or a paste in that in a stick, the formulated product can maintain its shape for extended time periods outside the package, the product not losing its shape significantly (allowing for some shrinkage due to solvent evaporation). Gels or pastes can be suitably packaged in containers which have the appearance of a stick, but which dispense through apertures on the top surface of the package. These products have been called soft sticks or "smooth-ons". Hereinafter, these soft sticks are generically called "gels". Reference is made to U.S. Pat. No. 5,102,656 to Kasat, U.S. Pat. No. 5,069,897 to Orr, and U.S. Pat. No. 4,937,069 to Shin, each of which discloses such gels, including physical characteristics thereof such as viscosity and hardness. The contents of each of these three U.S. Patents are incorporated herein by reference in their entirety.

Recently, there has been significant activity in developing clear and translucent antiperspirant sticks and gels. Clear or translucent antiperspirant sticks consisting essentially of a solution of the active antiperspirant material in a polyhydric alcohol vehicle, gelled by dibenzylidene monosorbitol acetal, have been disclosed. Clear and translucent antiperspirant gels (which have been dispensed from containers having the appearance of a stick) have been marketed, consisting of viscous, high internal phase emulsions. However, such conventional sticks and gels have drawbacks.

U.S. Pat. No. 5,500,209 (issued on Application Ser. No. 08/214,111), the contents of which are incorporated herein by reference in their entirety, discloses a gel or stick which includes active deodorant and/or antiperspirant ingredients, a polyamide gelling agent, and a solvent for the polyamide gelling agent, which gel or stick composition can be clear or translucent. This patent application discloses that the polyamide gelling agent is soluble in a cosmetically acceptable solvent at elevated temperatures, and solidifies (gels) upon cooling; acceptable solvents are disclosed as including various alcohols, including various glycols.

While the polyamide-containing stick or gel disclosed in the aforementioned U.S. Pat. No. 5,500,209 contains desirable properties in connection with stability of the composition, particularly in the presence of acidic antiperspirant active materials, and in providing clear or translucent gel or stick compositions, various attributes need to be improved. Specifically, the compositions according to U.S. Pat. No. 5,500,029, containing glycol solvents for the polyamide gelling agent and/or for the antiperspirant active material, may have a disadvantageous amount of tackiness and stickiness both upon and after application to the skin.

In general, various of the polyamides described in the aforementioned U.S. Pat. No. 5,500,209 are used commercially for thermal adhesive formulations, are very sticky in their molten phase, and are considerably tacky even in gel formulations, especially after the volatile solvent is evaporated. This property is very undesirable for cosmetic applications, particularly for antiperspirant and/or deodorant applications, because it produces formulations with an unpleasant sensation when applied to the skin.

Addressing this problem of tackiness and stickiness in connection with cosmetic compositions utilizing a polyamide gelling agent, U.S. patent application Ser. No. 08/426, 672, filed Apr. 21, 1995, the contents of which are incorporated by reference herein in their entirety, discloses use of a specific solvent system for a solid composition containing an antiperspirant active material and a polyamide gelling agent. This solvent system is glycol-free and contains a non-ionic surfactant and a polar solvent. Water is the polar solvent, and with the non-ionic surfactant acts as a dispersing medium for the antiperspirant active material, in which sufficient water is used to give a clear or translucent solution/emulsion of the antiperspirant active material.

Notwithstanding the foregoing, it is still desired to provide a solid cosmetic composition, containing a cosmetically active material in a sufficient amount so as to have a cosmetic effect, the composition being thickened using a polyamide gelling agent, the composition having improved cosmetic properties, including reduced tackiness and stickiness both upon and after application.

A typical technique to reduce the tackiness of, for example, antiperspirant formulations is the incorporation of cyclomethicone (such as a mixture of penta- and hexa-cyclodimethylsiloxanes). This cyclomethicone is a very low-viscosity liquid that provides excellent lubricity, which eliminates the tacky feeling. Cyclomethicone is also mildly volatile and therefore does not leave stains on the skin and/or clothing. More than 50% by weight of cyclomethicone has been incorporated into solid stick antiperspirant formulations, for example, using a wax solidifying agent. However, cyclomethicone is a nonsolvent for polyamides described as gelling agents in U.S. Pat. No. 5,500,029. Moreover, only limited quantities of the cyclomethicone (for example, 37% by weight) can be incorporated in solid compositions gelled using such polyamide gelling agent, without destroying the clarity of the gelled composition. Beyond that point, the gelled composition becomes cloudy because of either excessive crystallization of the polyamide or immiscibility of the cyclomethicone in the mixture.

U.S. Pat. No. 5,243,010 to Choi, et al., the contents of which are incorporated herein by reference in their entirety, discloses aromatic polyamide resins having pendant silyl groups, such resin having excellent heat-resistance, mechanical strength, electrical conductivity and other physical properties, as well as excellent solubility in common organic solvents and improved molten processing properties. This patent does not describe use of the aromatic polyamide resin as a gelling agent, much less as a gelling agent in cosmetic compositions to provide solid cosmetic compositions.

U.S. Pat. No. 5,272,241 to Lucarelli, et al., the contents of which are incorporated herein by reference in their entirety, discloses organofunctional siloxanes useful in both the personal care and plastics industries, the siloxanes being amino acid functionalized silicones. It is disclosed in this patent that the siloxanes have uses as plastic additives, hydraulic fluids, vibration damping agents, release agents, antifoamers, dielectric media, water repellents, surfactants, cosmetic and health product additives, lubricants, etc. This patent does not disclose use of the siloxanes as gelling agents.

Thus, it is an object to provide a gelling agent or co-gelling agent for such base composition and cosmetic and composition, as a thickening agent.

It is a further object of the present invention to provide a solid cosmetic composition (for example, a gel or stick composition), containing a cosmetically active ingredient and a gelling agent, which can be a clear composition, having reduced tack both upon and after application, and a method of forming the same.

It is a still further object of the present invention to provide a solid cosmetic composition, utilizing a gelling agent, and which has increased compatibility with silicone fluids (for example, cyclomethicone or dimethicone liquids), allowing creation of compositions which contain high levels of silicone fluids (such as these silicone oils), and a method of forming the same.

It is a still further object of the present invention to provide solid cosmetic compositions utilizing gelling agents, which compositions have improved cosmetic and application properties, including having reduced tackiness and stickiness, and a method of producing the same.

It is a still further object of the present invention to provide an antiperspirant and/or deodorant solid (for example, gel or stick) composition, containing deodorant and/or antiperspirant active materials, thickened using a gelling agent, which composition can be clear or at least translucent, the composition containing increased amounts of silicone fluids (for example, cyclomethicone and/or dimethicone) and having reduced tackiness and stickiness both upon and after application, and a method of making the same.

SUMMARY OF THE INVENTION

Accordingly, the present invention provides a base composition for a thickened (for example, solid) cosmetic composition in which a cosmetically active ingredient can be incorporated, utilizing as the thickening agent (also called the gelling agent) a composition comprising a wax containing silicon units and a polyamide gelling agent which itself optionally can also contain silicon units, which base composition and resulting cosmetic composition have improved application properties (including reduced tack), and a method of forming the same.

The foregoing objectives are achieved according to the present invention, by using, as at least part of the thickening agent, a wax with an amide thickening agent wherein at least the wax contains silicon moieties. This thickening agent enhances compatibility of a silicone fluid, such as cyclomethicone and/or dimethicone, in the composition, so that increased amounts of the silicone fluid can be included in the composition without adversely affecting other properties (for example, clarity) of the composition. For example, the base composition can include more than 50% of a silicone oil. Moreover, by incorporating increased amounts of the silicone fluid in the composition, tackiness and stickiness of the composition can be reduced.

In addition, various of the thickening agents having silicon-containing moieties per se, described below, provide a gel which is less tacky or sticky than, for example, various of the polyamide thickening agents described in the aforementioned U.S. Pat. No. 5,500,209, even without the increased amounts of silicone oil.

A solid cosmetic composition made according to the present invention includes a base composition made from a silicone fluid (for example a silicone liquid, such as a silicone oil) and a gelling agent made with a wax containing silicon units and an amide which optionally itself may also contain silicon units; and at least one cosmetic material. Optionally other solvents (which may also be silicon fluids), emollients, fillers, fragrance, antibacterials (antimicrobials), colorants and other ingredients known to those skilled in the art for formulating such products may be added. The thickening agent includes silicon-containing moieties to enhance compatibility of the silicone fluid in the composition.

In general, the active cosmetic material is included in an amount sufficient to have a cosmetically active effect. Depending on the active cosmetic material, various products can be provided. For example, the active cosmetic material can be a fragrance, an antiperspirant active material, a deodorant active material, a sunscreen, an insecticide, a colorant, etc. The resulting composition would be a perfume composition, an antiperspirant and/or deodorant composition, a sunscreen composition, an insect repellent, a lipstick, etc.

Compositions according to the present invention can be clear, or at least translucent, although compositions, containing the aforementioned thickening agent, which are not clear or translucent, are also contemplated as being within the scope of the present invention. Moreover, depending on the amount of thickening agent included in the composition, the solid composition formed can be a gel or a stick.

According to one particular embodiment of the present invention, the thickening agent includes a wax with a silicon portion and a polyamide gelling agent having silicon-containing moieties. For example, the polyamide portion of the gelling agent can be a copolymer formed from monomers or oligomers including a siloxane oligomer (for example, a copolymer formed by reacting an oligosiloxane diamine with a dimer acid). The polyamide gelling agent can also be a polyamide formed by silyl amidation or silyl esterification of dimer-based polyamides (for example, reacting free acid end-sites on an original polyamide with oligosiloxanes each containing at least one amine group, or with oligosiloxane alcohols or diols).

As a further aspect of the present invention, the polyamide portion of the gelling agent can be a polyamide formed by substituting an oligosiloxane diamine for the diamine in an original polyamide (transamidation at elevated temperatures such as at least 150 degrees C. and, more particularly, at least 200 degrees C.). The polyamide portion of the gelling agent can be a polyamide formed by grafting pendant oligosiloxane groups on an original polyamide.

The amide thickening agent having silicon-containing moieties can be a siloxane diamide wax, with the composition also containing a polyamide gelling agent as described in U.S. Pat. No. 5,500,209 as an additional embodiment of the thickening agents useful in this invention.

By incorporating thickening agents having silicon-containing moieties (for example, silicone (siloxane)-containing moieties), compatibility of a silicone fluid in the composition, as compared with compatibility of such fluid in a composition containing amide thickening agents which do not include the silicon-containing moieties, is enhanced. Accordingly, more silicone fluid (for example, more silicone oil) can be incorporated in the composition without disadvantageously affecting, for example, clarity of the composition such as in an amount of 10–15% more than the base amount. By incorporating more silicone fluid in the composition, cosmetic and application properties, including tackiness or stickiness, can be improved; that is, compositions according to the present invention have reduced tackiness and stickiness both upon application to the skin and while on the skin. Furthermore, not only does the increased amounts of silicone fluid achieve reduced tackiness and stickiness, the various amide thickening agents having silicon-containing moieties provide a gel and/or stick having reduced tackiness and stickiness, apart from the increased amount of silicone fluid in the composition.

Accordingly, the cosmetic composition of the present invention has improved application and cosmetic properties, while certain embodiments can still achieve a composition which can be clear.

DETAILED DESCRIPTION OF THE INVENTION

The present invention contemplates a base composition capable of being formulated into a cosmetic composition, for example, a solid cosmetic composition such as a gel or a stick. The base composition comprises a thickening agent and at least one solvent for the thickening agent, wherein: (1) the thickening agent comprises a silicon-containing wax and an polyamide itself optionally containing silicon moieties; and (2) the solvent comprises at least one silicone fluid whereby the compatibility of the silicone fluid in the base composition is enhanced. The thickening agent can be a wax having silicon-containing moieties such as dialkyl or diaryl siloxane repeat units where (a) the number of units "n" is 1–100; (b) each alkyl is independently selected from the group consisting of methyl, ethyl, propyl and isopropyl; and (c) each aryl is phenyl optionally substituted with 1,2 or 3 methyl or ethyl groups. The wax is mixed with a polyamide gelling agent to enhance such compatibility of the silicone fluid in the composition. The gelling agent is selected so that it is capable of dissolving in a fluid which contains silicone at a temperature of 25–150 degrees C. to form a translucent or clear solution at a temperature in this range. By soluble in silicone, we mean that the polymer can be dissolved in the silicone fluid at least at elevated temperature (but below the boiling point of the silicone fluid).The individual components required for the gelling agents can either be obtained commercially or can be prepared utilizing various techniques, as will be discussed below. The present invention also contemplates a solid cosmetic composition containing a cosmetically active ingredient in this vehicle.

The base composition formed from the polymers and the silicone fluids (optionally with the addition of other solvents) is then combined with at least one other active ingredient (which itself may need a further vehicle to be incorporated into the base composition) and other optional ingredients such as fragrance, emollients (especially silicone-miscible emollients), coloring agents, fillers, antibacterials (antimicrobials) and other conventional ingredients known to those in the art for formulating such products to form cosmetic compositions.

As another aspect of the present invention, the amide thickening agent can be a siloxane diamide wax or a partial siloxane diamine (both being referred to hereafter as siloxane diamide wax), used in combination with a polyamide gellant with or without silicon-containing moieties. Thus, according to this aspect of the present invention, the siloxane diamide wax is a co-former with the aforementioned polyamide gallant.

By siloxane groups we mean groups having siloxane units (for example, —Si($R^1$)($R^2$)—O—), where $R^1$ and $R^2$ are each independently selected from the group consisting of methyl, ethyl, propyl, isopropyl and phenyl wherein the phenyl is optionally substituted independently by 1, 2 or 3 of methyl and ethyl in the polymer. The siloxane units can be in the main chain, in pendent chains or in both the main chain and in pendant chains. The siloxane units occur in segments:

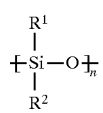

in the polymer where each segment of repeating siloxane units has a number "n" of siloxane units independently selected from the range 1–300, and more particularly from the range of 10–100.

The silicone fluids to be incorporated in compositions according to the present invention are those conventionally utilized in cosmetic compositions. These include linear siloxanes known as dimethicones, linear siloxanes containing an aromatic substitution such as phenyl trimethicone and the various cyclic siloxanes having from 4–6 members in a ring, particularly cyclic dimethyl siloxanes such as cyclomethicones. Mixtures of such silicone fluids may also be used. Suitable volatile silicone liquids are described in U.S. Pat. No. 5,102,656 to Kasat, referenced above. Examples of other known silicone fluids for use in cosmetic compositions are disclosed in U.S. Pat. No. 4,853,214 to Orr, referenced above and are suitable for this invention. Other particular examples include linear volatile silicone fluids, for example, silicone liquids conventionally used in cosmetic compositions.

While the present invention will be described in connection with specific and preferred embodiments, it will be understood that it is not intended to limit the invention to those embodiments. To the contrary, it is intended to cover all alterations, modifications and equivalents as may be included within the spirit and scope of the invention as defined by the appended claims.

Thus, throughout the present disclosure, the present invention is described primarily in connection with antiperspirant and/or deodorant compositions, including clear antiperspirant and/or deodorant gel and stick compositions. However, the present invention is not limited to such compositions; for example, the composition according to the present invention can be a sunscreen composition. Depending on active ingredients included in the composition, the composition can be an emollient composition, a perfume composition, etc. As to various types of solid cosmetic compositions and respective active materials which can be incorporated therein, which are applicable to the present invention, attention is directed to U.S. Pat. No. 4,322,400 to Yuhas, the contents of which are incorporated herein by reference in their entirety.

Throughout the present specification, "deodorant active" materials and "antiperspirant active materials" are discussed. Both types of materials contribute to reduction of body (for example, axillary) malodor. By reduction of body malodor, we mean that, generally, there is less body malodor after application of the composition to a person's skin, as compared to body malodor of the person without application of the composition. Such reduction can be due to a masking of the malodor, absorption and/or chemical reaction of the malodorous materials, reduction of levels of the bacteria producing the malodorous materials, for example, from perspiration, reduction of perspiration, etc. The antiperspirant materials, when utilized in appropriate amounts, act to reduce body malodor by reducing production of perspiration; the antiperspirant materials can also have a deodorant function, for example, as an antimicrobial agent. The deodorant active materials do not substantially reduce the production of perspiration, but reduce malodor in other ways, for example, as fragrances masking the malodor by reducing the malodor intensity, as odor absorbents, as antimicrobial agents, as agents chemically reacting with malodorous material, etc.

Throughout the present specification, where compositions are described as including or comprising specific components or materials, it is contemplated by the inventors that the compositions of the present invention also consist essentially of, or consist of, the recited components or materials. Accordingly, throughout the present disclosure any described composition of the present invention can consist essentially of, or consist of, the recited components or materials.

As indicated previously, the solid composition of the present invention can be a clear, or at least a translucent, gel or stick composition (for example, antiperspirant gel or stick composition). The term clear or transparent (that is, clarity), according to the present invention, is intended to connote its usual dictionary definition; thus, a clear cosmetic gel or stick allows ready viewing of objects behind it. By contrast, a translucent antiperspirant stick, although allowing light to pass through, causes the light to be so scattered that it will be impossible to see clearly objects behind the translucent stick. Opaque compositions do not allow a substantial amount of light to pass therethrough.

Within the context of the present invention, a gel or stick is deemed to be transparent or clear if the maximum transmittance of light of any wavelength in the range 400–800 nm through a sample 1 cm thick is at least 35%, preferably at least 50%. The gel or stick is deemed translucent if the maximum transmittance of such light through the sample is between 2% and less than 35%. A gel or stick is deemed opaque if the maximum transmittance of light is less than 2%. The transmittance can be measured by placing a sample of the aforementioned thickness into a light beam of a spectrophotometer whose working range includes the visible spectrum, such as a Bausch & Lomb Spectronic 88 Spectrophotometer. As to this definition of clear, see European Patent Application Publication No. 291,334A2.

The active cosmetic material can be those compatible with the thickening agent and solvent therefor. As mentioned previously, such active cosmetic materials can include, but are not limited to, deodorant and/or antiperspirant active materials, sunscreen materials, emollients, fragrances, insect repellents, etc.

Conventional antiperspirant metal salts can be incorporated in the composition of the present invention, as the antiperspirant active material. See the aforementioned U.S. Pat. No. 5,500,209, the contents of which have previously been incorporated herein by reference in their entirety, for a description of antiperspirant active materials (for example, antiperspirant metal salts, including aluminum salts) which can be incorporated in the composition of the present invention. The polyamide gelling agent, whether or not having the silicon-containing moieties, is stable in an acidic environment, so that the stability of the composition according to the present invention, in the presence of conventional acidic antiperspirant metal salts, is excellent.

In the base composition, the gelling agent can be used in an amount of 1–60 percent by weight, more particularly 5–30 percent by weight and most particularly 10–20 percent by weight. It is preferred that the gellant not exceed 50 percent by weight of the base composition. The silicone fluid portion is in the range of 0.5–95 percent by weight, more particularly 10–80 percent by weight, even more particularly 20–75 percent by weight and most particularly 30–70 percent by weight. Examples of such silicon fluids include cylcomethicone and dimethicone. Optionally, additional solvent or mixtures of solvents may be added to form the base composition. Suitable additional solvents are those which are either themselves or in mixtures with other solvents miscible in the originally selected silicone. Examples of additional solvents include cosmetic esters (for example, the C12–15 lactate ester known as Ceraphyl 41), guerbet alcohols having 8–30 carbons, particularly 12–22 carbons (for example, isolauryl alcohol, isocetyl alcohol, isostearyl alcohol), fatty alcohols (for example, stearyl alcohol, myristyl alcohol, oleyl alcohol), ethanol, and ethoxylated alcohols (for example, the polyethylene glycol ether of lauryl alcohol that conforms to the formula $CH_3(CH_2)_{10}CH_2(OCH_2CH_2)_nOH$ where n has an average value of 4 (also called laureth-4)). Other examples include (a) PPG-14 butyl ether, where the "PPG-14" portion is the polymer of propylene oxide that conforms generally to the formula $H(OCH_2C(CH_3)H)_NOH$, where n has an average value of 14; (b) isopropyl myristate; (c) PPG-2 myristyl ether propionate which is the ester of propionic acid and the polypropylene glycol ether of myristyl alcohol that conforms to the formula $CH_3(CH_2)_{12}CH_2(OCH(CH_3)CH_2)_2O—C(O)CH_2CH_3$; and (d) PPG-13 myristyl e the polypropylene glycol ether of myristyl alcohol that conforms to the formula $CH_3(CH_2)_{12}CH_2(OCH(CH_3)CH_2)_nOH$ where n has an average value of 13 By using the base and cosmetic compositions of the present invention the upper range of the amounts of silicone fluids which can be incorporated in the gel is higher than amounts which can be incorporated in conventional compositions.

Optionally, additional solvent or mixtures of solvents may be added to form the base composition. Suitable additional solvents are those which are either themselves or in mixtures with other solvents miscible in the originally selected silicone fluid (for example, C14–C20 fatty alcohols, isopropyl myristate, adipate palmitate and isostearate). By using the base and cosmetic compositions of the present invention, the upper range of the amounts of silicone fluids which can be incorporated in the gel is higher than amounts which can be incorporated in conventional compositions.

The base composition is then mixed with the other ingredients listed elsewhere so that the final cosmetic composition can be made, Such additional ingredients can be used in amounts of 0.5–85 percent, more particularly 1–75 percent and even more particularly 2–55 percent where the percentages are based by weight on the base composition as 100 percent. The lower percent ranges include formulations where only fragrances are used and the upper ranges include formulations containing active antiperspirant ingredients. An antiperspirant active itself (excluding any vehicle for adding the active to the formulation) can be present in the final cosmetic formulation in an amount of from 5–25 percent.

While siloxane units have been defined above, more particular values for $R_1$ and $R^2$ are methyl, ethyl and phenyl and an even more particular value for each of $R_1$ and $R^2$ is methyl.

While various silicone fluids have been described above, particular silicone fluids useful in the invention include cyclomethicone, dimethicone and phenyltrimethicone.

Various antiperspirant active materials, which may be mentioned by way of example (and not of a limiting nature), including aluminum chlorohydrate, aluminum chloride, aluminum sesquichlorohydrate, zirconyl hydroxychloride, aluminum-zirconium hydroxychlorides, aluminum-zirconium glycine complex (for example, aluminum-zirconium tetrachlorohydrex-Gly and aluminum-zirconium octachlorohydrex-Gly), aluminum chlorohydrex PG, aluminum chlorohydrex PEG, aluminum dichlorohyrex PG and aluminum dichlorohyrex PEG can be utilized as the antiperspirant active material in compositions according to the present invention. The compositions according to the present invention need not include aluminum containing metal salts, and can include other antiperspirant active materials, including other antiperspirant active metal salts. Generally, Category I active antiperspirant ingredients listed in the Food and Drug Administration's Monograph on Antiperspirant Drug Products for Over-The-Counter Human Use (Oct. 10, 1993) can be used. In addition, any new drug, not listed in this Monograph, such as aluminum nitratohydrate and its combination with zirconyl hydroxychlorides and nitrates, or aluminum-stannous chlorohydrates, can be incorporated as an antiperspirant active ingredient in antiperspirant compositions according to the present invention.

The antiperspirant active can be incorporated into compositions according to the present invention in amounts in the range of 0.1–30%, preferably 15–25%, by weight, of the total weight of the composition. At amounts in the lower end of the broader range (for example, 0.1–10%), the antiperspirant active material will not substantially reduce the flow of perspiration, but will reduce malodor, for example, by acting as an antimicrobial material.

Where deodorant active materials are incorporated in compositions according to the present invention, so as to provide deodorant compositions, conventional deodorant fragrances and/or antimicrobial agents can be incorporated as the deodorant active materials. A fragrance would, illustratively, be incorporated in an amount of 0.5%–3.0% by weight, of the total weight of the composition; the antimicrobial/bacteriostat material, such as Triclosan, can illustratively be included in an amount of from 0.1% to about 0.5% by weight, of the total weight of the composition.

Cosmetic compositions according to the present invention include both a thickening agent and a solvent for the thickening agent (in the present application, the thickening agent and solvent for the thickening agent provide a vehicle for the active cosmetic material, and have been so designated as a vehicle).

The solvent for the thickening agent is included in the composition in an amount sufficient such that the thickening agent can be dissolved therein and gelled therefrom, and includes a silicone fluid (for example, a silicone oil, such as cyclomethicone and/or dimethicone). The thickening agent can be dissolved in the solvent and gelled therefrom, for example, upon cooling the composition during manufacture thereof.

The solvent is not limited to only containing a silicone fluid, and can contain other solvents for the thickening agent as long as such other solvents are compatible with, for example, the active cosmetic material and do not disadvantageously affect, for example, clarity of the composition, especially where it is desired to provide a clear cosmetic composition. For example, as defined in the CTFA International Cosmetic Ingredient Dictionary (4th Ed. 1991), an additional solvent included in the composition can be C12–15 alkyl lactate (which is an ester of lactic acid and C12–15 alcohols); this C12–15 alkyl lactate is vended by Van Dyk & Co., Inc. as "Ceraphyl 41". Solvents for the polyamide gelling agent, disclosed in U.S. Pat. No. 5,500,209 can be used in compositions of the present invention. The solvent for the antiperspirant active can be included in the composition in an amount within the range of 0–75 percent, preferably 0–25 percent, by weight, of the total weight of the composition.

Illustratively, and not to be limiting, the solvents can include esters (for example, the C12–15 lactate ester described above as Ceraphyl 41), silicone fluids (for example, cyclomethicone, dimethicone), guerbet alcohols having 8–30 carbons, particularly 12–22 carbons (for example, isolauryl alcohol, isocetyl alcohol, isostearyl alcohol), fatty alcohols (for example, stearyl alcohol, myristyl alcohol, oleyl alcohol), ethanol, and ethoxylated alcohols (for example, the polyethylene glycol ether of lauryl alcohol that conforms to the formula $CH_3(CH_2)_{10}CH_2(OCH_2CH_2)_nOH$ where n has an average value of 4 (also called laureth-4)). Other illustrative solvents include (a) PPG-14 butyl ether, where the "PPG-14" portion is the polymer of propylene oxide that conforms generally to the formula $H(OCH_2C(CH_3)H)_nOH$, where n has an average value of 14;

(b) isopropyl myristate;

(c) PPG-2 myristyl ether propionate which is the ester of propionic acid and the polypropylene glycol ether of myristyl alcohol that conforms to the formula $C_3(CH_2)_{12}CH_2(OCH(CH_3)CH_2)_2O—C(O)CH_2CH_3$; and (d) PPG-13 ether which is the polypropylene glycol ether of myristyl alcohol that conforms to the formula $CH_3(CH_2)_{12}CH_2(OCH(CH_3)CH_2)_nOH$ where n has an average value of 13. Mixtures of solvents can also be used. Of course, the gelling agent must be soluble in the solvent system, at least at elevated temperatures, as described in U.S. Pat. No. 5,500,209. Mixtures of solvents can also be used. Of course, the gelling agent must be soluble in the solvent system, at least at elevated temperatures, as described in U.S. Pat. 5,500, 209.

Compositions according to the present invention desirably include silicone-miscible emollients. Illustrative emollients, which are not limiting of the present invention, would include guerbet alcohols (such as isocetyl alcohol or isostearyl alcohol): esters (such as isopropyl palmitate, isopropyl isostearate, octyl stearate, hexyl laurate and isostearyl lactate); a liquid mixture of hydrocarbons which are liquids at ambient temperatures (such as petroleum distillates and light mineral oils); and ethanol. The silicone-miscible solvents (also called emollients) can be included in the compositions of the present invention in amounts within the range of 0–70%, preferably 0–25%, by weight, of the total weight of the composition.

Where a multi-phase system is utilized as the composition of the present invention, preferably the composition includes a surfactant or surfactant blend. Surfactants illustratively include alkanolamides (such as N-alkyl pyrrolidone), ethoxylated amides (for example, the polyethylene glycol amide of tallow acid that conforms generally to the formula $RC(O)—NH—(CH_2CH_2O)_nH$ where RCO— represents the fatty acids derived from tallow and n has an average value of 50 (also called PEG-50 tallow amide)); amine oxides (for example, cocamidopropylamine oxide); ethoxylated carboxylic acids (for example, the polyethylene glycol diester of lauric acid that conforms generally to the formula $CH_3(CH_2)_{10}C(O)—(OCH_2CH_2)_nO—C(O)(CH_2)_{10}CH_3$ (also called PEG-8 dilaurate)); ethoxylated glycerides (for example, a polyethylene glycol derivative of castor oil with an average of 4 m of ethylene oxide (also called PEG-4 castor oil)); glycol esters (for example, propylene glycol ricinoleate); monoglycerides (for example, glycerol myristate); polyglyceryl esters (for example, polyglyceryl-4 oleyl ether); polyhydric alcohol esters and ethers (for example, sucrose distearate); sorbitan/sorbitan esters (for example, sorbitan sesquiisostearate); triesters of phosphoric acid (for example, trioleth-8 phosphate (a material which is predominantly the triester of phosphoric acid and ethoxylated oleyl alcohol with an average of 8 moles of ethylene oxide)); ethoxylated alcohols (for example, laureth-4); ethoxylated lanolin (for example, a polyethylene glycol derivative of Lanolin with an average of 20 moles of ethylene oxide (also called PEG-20 lanolin)); ethoxylated polysiloxanes (for example, dimethicone copolyol); propyloxated polyoxyethylene ethers (for example, the polyoxypropylene, polyoxyethylene ether of cetyl alcohol that conforms generally to the formula $CH_3(CH_2)_{14}CH_2(OCH(CH_3)CH_2)_x(OCH_2CH_2)_yOH$ where x has an average value of 5 and y has an average value of 20 (also called PPG-5 ceteth-20)); and alkylpolyglycosides (for example, lauryl glucose). The surfactant (or surfactant blend) includes non-ionic compounds, and can also include blends thereof with cationic (for example, the polyethylene glycol amine of tallow acid that conforms generally to the formula $R—NH—(CH_2CH_2O)_nH$ (n=15, also called PEG-15 tallow amine)) or anionic (for example, sodium lauryl laurate which is the sodium salt of the lauric acid ester of lauric acid) surfactants.

The surfactant or blend thereof incorporated in compositions according to the present invention can, illustratively, be included in amounts of 0–15%, preferably 0–4%, by weight, of the total weight of the composition.

As indicated previously, the compositions according to the present invention can be creams (semi-solids or soft-solids), gels or sticks, depending on amounts of thickening agent incorporated in the composition. It is difficult to quantitatively distinguish between a cosmetic "gel" and a cosmetic "stick". Generally, a gel is more viscous than a liquid or than a paste which fails to retain its shape; however, it is not as rigid as a stick. Typically, it is understood that gels are soft, deformable products while sticks are free-standing solids. In the cosmetic field, systems are classified as gels or sticks depending on their viscosity or hardness alone; typically, it is understood that gels are soft, deformable products while sticks are strictly free-standing solids. For example, by Theological analysis, a commercial deodorant stick has been determined to have a plateau storage modulus $G^1(\omega)$ of roughly $10^5$ Pa and a complex viscosity of $10^6$ Pa second (both at an angular frequency of 0.1 rad-sec). On the other hand, a commercial antiperspirant gel has been determined to have a $G^1(\omega)$ value of roughly $10^3$ Pa and a complex viscosity of $10^4$ Pa second (at 0.1 rad-sec).

The thickening agent includes an amide thickening agent which has silicon-containing moieties. According to one aspect of the present invention, such amide thickening agent can include a polyamide gelling agent having silicon-containing moieties. Such silicon-modified polyamide can be formed by a copolymerization technique, which involves polymerizing the polyamide from monomers which include a siloxane monomer. For example, the silicon-modified polyamide can be a copolymer which is the product of copolymerization of a dicarboxylic acid with diaminosiloxane oligomers.

An illustration of such copolymerization utilizes an oligosiloxane which is terminated at both ends with a-aminopropyl groups. Such an oligosiloxane is called a siloxane diamine, a diamino siloxane oligomer, or alpha, omega-bis (aminopropyl) oligodimethylsiloxane. Such oligomers would have the following structure:

$H_2NCH_2CH_2CH_2—(CH_3)_2Si—(OMe_2Si)_n—O(CH_3)_2SiCH_2CH_2CH_2NH_2$, where n is an average value and varies from 1–300, more particularly from 10–100, even more particularly from 10–40 and especially from 10–30; and Me is methyl. This monomer is available at various average lengths from United Chemical Technologies (Bristol, Pa.), Wacker Silicones (Adrian, Mich.), Shin Etsu (Tokyo, Japan) and Gelest (Tullytown, Pa.).

The copolymer can include the siloxane diamine as the sole diamine material in forming the copolymer, or preferably the copolymer can also include additional diamine (such as ethylene diamine and/or hexamethylene diamine). Including such additional diamine would aid in producing a solid polymer, which can be useful in gelling fluids. Desirably, the siloxane diamine has n equal to at least 10, so as to provide better products.

Preferably, the number of repeating siloxane units ("n" in the above formula) ranges between 10 and 30. Siloxanes with low "n" are relatively expensive, while siloxanes with high "n" (n greater than 30) will be hard to react.

Generally, the copolymers are produced utilizing the following Reaction Scheme I:

REACTION SCHEME I

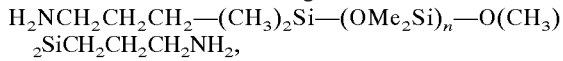

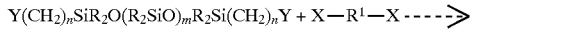

where:
n is an average value and is selected to be in the range of 2–10, preferably 3–6;
R at each occurrence is independently selected from the group consisting of methyl, ethyl, propyl, isopropyl and phenyl wherein the phenyl may optionally be substituted by 1–3 of a member of the group consisting of methyl and ethyl; more particular values for R are methyl, ethyl and phenyl, especially methyl;

$R_1$ is selected from the group consisting of (a) a straight or branched alkyl chain having 1–40 carbons, particularly 2–20 carbons and especially 2–6 carbons optionally substituted by at least one of methyl, ethyl, propyl, isopropyl, hydroxy, carboxyl and phenyl groups wherein the phenyl may optionally be substituted by 1–3 of a member of the group consisting of methyl and ethyl, wherein the alkyl chain may optionally contain at least one an alkenyl bond and (b) an alkyl chain containing at least one cyclic or phenyl group wherein said chain has 7–40 carbons, particularly 7–20 carbons, and may optionally be substituted by at least one of methyl, ethyl, propyl, isopropyl, hydroxy, carboxyl and phenyl groups wherein the phenyl may optionally be substituted by 1–3 of a member of the group consisting of methyl and ethyl, wherein the alkyl chain may optionally contain at least one alkenyl bond;

$X=NH_2$ when $Y=CO_2H$ and $X=CO_2H$ when $Y=NH_2$.

Thus, as seen in the foregoing reaction, the silicone-containing monomer can be either the diacid or the diamine.

Mixtures of diacids (dicarboxylic acids) as well as mixtures of diamines can be used in the polymerization. Illustrative diacids for making the copolymer include dimer acids (hydrogenated or non-hydrogenated), adipic acid, butanedioic acid, tartaric acid, gluconic acid, oxalic acid, diglycolic acid, malonic acid, succinic acid, glutaric acid, malic acid, maleic acid, dodecanedioic acid, terephthalic acid and isophthalic acid, and mixtures. If a silicon-based dicarboxylic acid is used, a variety of diamines could be used to make the polyamide (for example, ethylene diamine, hexamethylene diamine, piperizine, phenylenediamine, etc.).

Alternatively, the silicon-containing polyamide gelling agent can be produced by silyl amidation of dimer-based polyamides. This approach involves the reaction of free acid sites existing on an original polyamide as terminal sites, with oligosiloxane-amines and/or oligosiloxane-diamines (amidation reaction), or alternatively with oligosiloxane-alcohols or oligosiloxane-diols (esterification reaction). The esterification reaction requires the presence of acid catalysts, as known in the art. It is desired that the polyamide having free acid sites, utilized for the amidation or esterification reaction, have a relatively large number of acid end groups (for example, polyamides with high acid numbers of, for example, 15–20).

For the amidation of free acid sites of polyamides, illustratively (and not to be limiting) siloxane diamines with n (siloxane groups) equal to 1–300, more particularly 2–50 and even more particularly selected from the group consisting of 2, 6, 9.5, 12, 13.5, 23 and 31 can be used for reaction with dimer-based polyamides, where n is an average number. Best results have been achieved with the siloxane diamine having n=13.5, and with polyamides containing high levels of carboxylic acid end-groups. Reactions were performed either in xylene to extract produced water from the solution by azeotropic distillation, or at higher temperatures (around 180° C. –200° C.) without solvents. Typically, the efficiency of the amidation and reaction rates decrease when the siloxane diamine is longer (higher n). Free amine sites can be capped after the initial amidation reaction of diaminosiloxanes by reacting with either siloxane acid or an organic acid such as benzoic acid.

For the esterification of free acid sites on polyamides, this can be performed in boiling xylene with about 1% by weight (of the total weight of the reaction materials) para toluene sulfonic acid as catalyst.

In the amidation of the free acid sites, cyclomethicone incorporation ability increases as the number of siloxane groups/amide group increases, as shown below in Table A:

TABLE A

| siloxane groups/amide group | maximum % of cyclomethicone in solvent resulting in clear gels |
|---|---|
| 0 | 40 |
| 0.5 | 55 |
| 1.3 | 55 |
| 2.6 | 59 |

An example of this amidation is shown in the following Reaction Scheme II:

REACTION SCHEME II $R^2+[(CH_3)_2SiO]_n-(CH_3)_2Si(CH_2)_3NH_2 +$

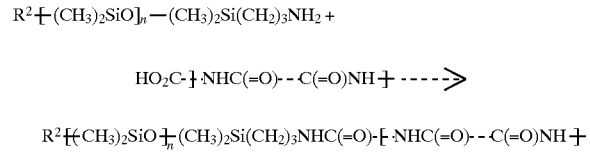

$R^2+[(CH_3)_2SiO+_n(CH_3)_2Si(CH_2)_3NHC(=O)+NHC(=O)--C(=O)NH+$ where $R^2$ is selected from the group consisting of hydrogen, methyl, ethyl, propyl and isopropyl, butyl, and straight chain and branched amino alkyls having 1–4 carbons (particularly aminopropyl); and n is an average value and is selected to be 1–40, particularly 1–30, more particularly 1–25, with a particular group being a value selected from the group consisting of 1, 2, 3, 7, and 21. The product of this reaction provides a polyamide backbone with siloxane termination sites.

In these reactions, silicone moieties are incorporated only at the chain ends. The resulting polymers have relatively large compatibility with silicone fluids, the enhanced compatibility being greater when the starting (original) polyamides have high acid numbers.

Illustratively, but not limiting, the original polyamide can be a dimer based polyamide hot melt adhesive resin such as Unirez 2973, from Union Camp Corp. This polyamide has 5% to 10% free acid sites.

If siloxane diamines are used (that is, an amidation reaction is used), a free amine group is incorporated into the polymer. This free amine group can be reacted with various organic or silicone-based carboxylic acids (for example, disiloxane-dipropionic acid) to produce another amide bond. It is thought that the final product should not have free amine sites, because these groups may result in lower product stability.

Preferably, the silicone-modified polyamide formed by this silyl amidation is obtained by reacting high acid polyamide with oligosiloxane diamines having an average from 10 to 13 repeating siloxane units. The reactants were refluxed in xylene using a reaction assembly consisting of a azeotropic finger to constantly extract the generated water.

If the original polymer (polyamide) contains free amine sites, rather than free acid sites the siloxane reagent should contain an acid group instead of the amine to enable the amidation reaction.

As a third alternative for providing the silicon-modified polyamide gelling agent, an original polyamide having, for example, an ethylene diamine component is reacted with an oligosiloxane diamine at elevated temperatures (for example, 200° C. to 300° C.) so as to perform transamidation whereby the ethylene diamine component in the original polyamide is replaced by the oligosiloxane diamine. It is preferred that the level of replacement be at most 50%, so as to limit reduction of the gelation capability by the polyamide. Polyamides modified by transamidation in this way exhibit greater compatibility with silicone fluids (for example, clear gel compositions can be produced in which the solvent system is approximately 60% cyclomethicone).

For performing the transamidation, illustratively the original polyamide can be polyamides as described in U.S. Pat. No. 5,500,209, referred to previously, or a polyamide with a high acid number. The transamidation takes place at temperatures above 200° C. When higher temperatures are used, reaction time is very short (for example, 0.5 hours to 300° C.). Siloxane diamines with n (average number of siloxane groups) from 10 to 15 are most suitable for these reactions. Free amine sites formed during the transamidation can be capped by reaction with either siloxane carboxylic acid or an organic acid such as benzoic acid. Polyamide chains can also be broken during the transamidation. The polymer products obtained are not as hard as those formed by end-site amidation reactions; however, they are less sticky. This reaction is very simple and easily controlled.

A still further alternative approach to form the silicon-modified polyamides is the reaction of polysiloxanes bearing amino or alpha-carboxy groups which can react with organic acids or amines respectively to provide a polyamidosiloxane, having oligosiloxane groups. Aminopropyl siloxane copolymers, as the original polymer to be reacted with an organic acid, are commercially available. This approach is illustrated in the following Reaction Scheme III:

REACTION SCHEME III

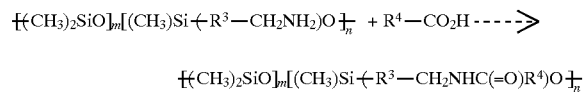

where
- R$^3$ is selected from the group consisting of —NH—; straight and branched chain C2–C40 alkylenes optionally containing at least one double bond or phenylene group, and where R$^3$ is particularly C1–C20, more particularly C2–10, and even more particularly ethylene;
- R$^4$ is selected from the group consisting of C1–C40 straight and branched chain C1–C40 alkylenes optionally containing at least one double bond or phenylene group, and where R$^4$ is particularly C1–C10; and
- n and m are average values and are each independently selected from the group 1–1000, articularly 1–100 and more particularly 1–50.

The polymer skeleton in this case is based on siloxane monomeric units and the amide groups are pendant.

In addition to the foregoing, original polyamides (not containing silicon moieties) can be modified, with the modified polyamides utilized in the composition of the present invention as the polyamide gelling agent, by grafting the polyamide with pendant oligosiloxane groups.

This can be done in many ways, including (but not limited to):

(a) hydrosilylation of unsaturated bonds in non-hydrogenated dimer-based polyamides;

(b) silylation of the amide groups in polyamides; and (c) silylation of unsaturated polyamides via oxidation.

The substitution by hydrosilylation reaction of unsaturated functional groups found in the polymeric skeleton as integral species of the dimer acid used as the copolymeric unit in the polyamide provides very stable Si—C bonds. This approach is shown by the following Reaction Scheme IV:

REACTION SCHEME IV

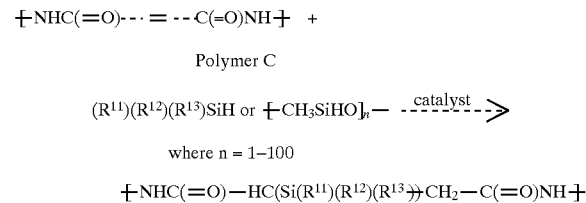

where each of R$^{11}$, R$^{12}$ and R$^{13}$ are independently selected from the group consisting of methyl, ethyl, propyl, isopropyl, butyl, isobutyl, phenyl and a siloxyl group of Formula IV:

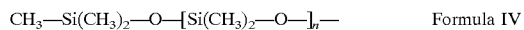    Formula IV where n is an average value and is selected to be in the range of 1–100.

Examples of suitable values for "(R$_{11}$)(R$^{12}$)(R$^{13}$)SiH" are, illustratively: (CH$_3$)$_3$SiH, (CH$_3$)$_{11}$Ph$_{3-n}$SiH, (CH$_3$)$_3$SiO—[(CH$_3$) $_2$SiO]$_n$—(CH$_3$)$_2$SiH, and (CH$_3$)$_k$Bu$_{3-k}$SiH, where k=0,1,2, or 3 and (CH$_3$)$_3$—Si—O—[CH$_3$SiHO]$_n$—(CH$_3$)$_2$SiH.

Examples of suitable values for catalysts are organometallic catalysts such as: H$_2$PtCl$_6$(Ru$_3$(CO)$_{12}$,(Ph$_3$P)$_3$RhCl, and others which have the effect of lowering the activation energy of the reaction.

In the present situation (hydrosilylation of unsaturated bonds), as well as in the other reaction schemes described herein, the R groups of the silylated compounds, and the number of substitutions on the polymer, can affect polymer properties (for example, lubricity, crystallinity).

In forming polyamides by hydrosilylation of unsaturated bonds, it is preferred to use original polyamides having higher concentrations of unsaturation. This can accomplished by forming the original polyamide using a highly unsaturated dimer acid, or using various diacids (such as itaconic acid, malic acid, maleic acid, etc.) which contain reactive groups, or by end-capping with an unsaturated mono-acid (such as linoleic acid). In these cases, the polymers are first reacted with siloxane amines or alcohols to eliminate any free acid sites, and then completely dried. After these steps, the hydrosilylation is performed.

As mentioned previously, the silicon-containing polyamide gelling agents utilized in the present invention can be formed by silylation of amide groups in original polyamides. This provides substitution on the amide functional sites. This substitution on the amide functional sites is by catalytic reaction between hydridosiloxane and the amide, which can lead to the formation of three potential substituted arrangements, as shown in the following Reaction Scheme V:

REACTION SCHEME V

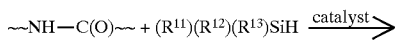

gives the following possible products at that reaction site:

—NH—CH[O—Si($R^{11}$)($R^{12}$)($R^{13}$)]—; —C(O)N—Si—($R^{11}$)($R^{12}$)($R^{13}$)—; and —N═C[O—Si($R^{11}$)($R^{12}$)($R^{13}$)]—.

While silylation of the amide groups improves compatibility with the silicone oils, destruction of the amide groups reduces gelation capabilities.

In addition, the silicon-modified polyamides can be formed by silylation of unsaturated polyamides via oxidation. That is, the unsaturated groups can be oxidized to alcohols or diols and then the newly developed hydroxyl groups can be reacted with either siloxane carboxylic acids or siloxane alcohols. Alternatively, the olefinic sites of the unsaturated polyamides can be epoxidized, followed by typical epoxy-ring opening with siloxane amines or siloxane alcohols.

As described previously, the thickening agents according to the present invention can include a siloxane diamide wax and polyamide gelling agent, the wax acting as a co-former thickening agent. The diamide wax can be formed, for example, by reacting two or more equivalents of stearic acid with a, w-bis (aminopropyl) oligodimethylsiloxane, according to the following Reaction Scheme VI:

REACTION SCHEME VI $H_2N(CH_2)_3$—$(CH_3)_2Si(O(CH_3)_2Si)_n(CH_3)_2Si(CH_2)_3NH_2$ +

2$R^{16}CO_2H$ ---->

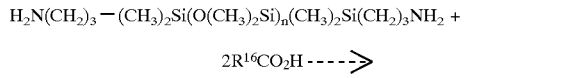

where $R^{16}$ is a $C_1$–$C_{40}$ aliphatic straight or branched chain group, particularly C1–C18; examples of suitable values for $R^{16}$ include stearyl, oleyl, lauryl and ethyl; and n is an average value and is selected from the range 1–1000, particularly 1–100 and more particularly 1–50.

The amine groups need not all be reacted in forming the diamine wax; that is, it can be acceptable to have diamine compound reacted only partially, leaving some free amine groups in the siloxane diamide wax.

Illustratively, stearic acid, oleic acid, lauric acid or acetic acid can be used as the carboxylic acid in the foregoing, and the oligosiloxane length in the diamide unit can preferably range from 2 to 32.

Compositions according to the present invention contain a sufficient amount of the thickening agent such that the final cosmetic composition is a solid composition, for example, a gel or stick.

Illustratively, compositions according to the present invention include, in percent by weight of the total weight of the composition, 10%–95% solvent and 2%–40% siliconized polyamide gelling agent. For compositions according to the present invention containing the siloxane diamide wax co-gellant, illustrative amounts of the components in the composition (in percent by weight, of the total weight of the composition) include 10%–95% solvent, 2%–40% gelling agent (for example, dimer-based polyamide gelling agent), and 1%–20% siloxane diamide wax co-gellant. In either case, and illustratively (and not limiting), the silicone fluid solvent is preferably included in the composition in an amount of 1%–95%, more preferably 30%–95%, most preferably 50%–95%, by weight, of the total weight of the composition.

The composition according to the present invention can include other ingredients conventionally incorporated in solid cosmetic compositions, for example, deodorant or antiperspirant gels and/or sticks, particularly if clarity is not a factor. These other ingredients could include an active phase (which may include water or glycol), waxes, other thickeners, surfactants, stabilizers, color and fragrance. As for various other ingredients which can be incorporated, attention is directed to the optional components such as hardeners, strengtheners, chelating agents, colorants, perfumes, emulsifiers and fillers, described in the various patent documents listed in the following, all incorporated by reference herein in their entirety: U.S. Pat. No. 3,255,082 to Barton; U.S. Pat. No. 4,049,792 to Elsanu; U.S. Pat. No. 4,137,306 to Rubino, et al.; and U.S. Pat. No. 4,279,658 to Hooper, et al.

Attention is also directed to U.S. Pat. No. 5,500,209, the contents of which have previously been incorporated herein by reference in their entirety, for various optional components, and amounts thereof, which can be incorporated in the composition of the present invention.

Where the composition is a deodorant composition, or an antiperspirant composition, deodorant active materials can be incorporated so as to provide deodorant active materials combatting body malodor. For example, a fragrance and/or antimicrobial agent can be incorporated. Fragrances and/or antimicrobial agents are incorporated in conventional amounts.

The degree of freedom in incorporating optional ingredients is increased, where a clear composition is not being formed (for example, where a translucent composition, or, especially, where an opaque composition, is being formed).

Compositions according to the present invention can be made by mixing the various components at an elevated temperature (that is, by heating and mixing the various components) and then cooling in order to form the gelled (solidified) composition, for example, as a gel or stick. Desirably, any volatile components (such as fragrances) are added to the mixture at a relatively late stage of the mixing, so as to limit volatilization of the volatile components. Generally, the solvent and thickening agent (including polyamide gelling agent) are mixed and heated so as to fully dissolve the thickening agent in the solvent. An active ingredient (for example, antiperspirant active material, for example, in dry form or as part of a solution) can be added after the thickening agent fully dissolves, and mixing then takes place. Mixing continues with cooling, with, for example, colorant and fragrance then being added. Thereafter, the resulting composition, still liquid, is poured into canisters, for example, dispensing packages, and solidified, as with conventional stick and gel compositions.

The compositions according to the present invention are used in the same manner as conventional gel or stick compositions, dispensed from, for example, dispensing containers. For example, the gel or stick, exposed out of the dispensing package, is rubbed on skin, so as to deposit the active material (for example, antiperspirant and/or deodorant active materials) on the skin.

Illustratively, where a composition is an antiperspirant composition containing an antiperspirant active material for reducing perspiration in the axillary regions, and exposed portion of the composition is rubbed against axillary regions of the human body, so as to deposit the antiperspirant active material and, if present, deodorant active material, on the skin in the axillary region. The composition, both during the deposition on the skin and after application, has reduced tackiness and stickiness, as discussed previously.

In the following, illustrative contemplated examples of compositions within the scope of the present invention are set forth. These contemplated examples are illustrative of the present invention, and are not limiting. Amounts of components in these examples are in weight %, of the total weight of the composition.

In the following examples, as well as throughout the present specification, various names utilized are the CTFA (Cosmetics, Toiletries and Fragrance Association, Inc.) names, as set forth in the CTFA International Cosmetic Ingredient Dictionary (4th Ed. 1991).

The following Table B shows specific silicon-modified polyamide gellants and amide wax co-gellants. Examples 2 and 3 form amide wax co-gellants of this invention. Examples 1, 4 and 5 are Examples illustrated for comparison and are covered in a separate co-pending application.

TABLE B

| Example | Reagent (gm/gm of PA) | Catalyst or Additive Quantity | Extent of Reaction[a] (%) | Siloxane Units per Amide |
|---|---|---|---|---|
| 1 | $HSi(CH_3)_2OSi(CH_3)_3/0.30$ | $Ru_3(CO)_{12}$/5 mg | 3.2 | 0.06 |
| 2 | $[H_2N(CH_2)_3Si(CH_3)_2]_2O$ (0.5$_g$)[b] | stearic acid | 84.7 | 0.85 |
| 3 | $[H_2N(CH_2)_3Si(CH_3)_2]_2O$ (0.5$_g$)[b] | acetic acid | 91.6 | 0.92 |
| 4 | $HSi(CH_3)_2OSi(CH_3)_3/(0.88\ g)$ | $Ru_3(CO)_{12}$/15 mg | 35.1 | 0.70 |
| 5 | $[H_2N(CH_2)_3Si(CH_3)_2O\text{-}Si(CH_3)_2]_2O$ (0.5)[b] | | 4.3 | 0.17 |

[a] mole % of additive calculated based on the NMR integration comparison between the $Si(CH_3)$ group and —$CH_3$ group of the PA.
[b] mol ratio relative to counter acid.

TABLE C shows formulation of Examples 1–5 from Table B in various solutions. In Table C, C41 is Ceraphyl 41 and, together with the cyclomethicone, is a solvent for the formulations shown One (1) gram of each formulation was used, except for those in a formulation weight ratio of "(0.5/1.0)", which contained 1.5 grams of the formulation. In these examples, the polyamide (PA) used was Unirez 2973.

TABLE C

| Formulation[a] (includes polyamide or wax of specified Example of Table B) | C-41 (gm) | Cyclomethicone (gm) | Observation |
|---|---|---|---|
| Ex. 1 | 5.4 | 5.4 | clear gel |
| Ex. 1 | 5.4 | 6.0 | slightly cloudy |
| Ex. 1 | 6.0 | 6.0 | almost clear |
| Ex. 4/PA[b] (0.5/0.5) | 5.4 | 5.0 | clear gel |
| Ex. 4/PA (0.5/0.5) | 6.0 | 6.0 | very slightly cloudy |
| Ex. 2/PA (0.5/0.5) | 5.4 | 6.5 | almost clear; hard |
| Ex. 2/PA (0.5/1.0) | 8.5 | 9.5 | almost clear; hard |
| Ex. 2/PA (0.5/0.5) | 4.5 | 5.3 | clear; hard |
| Ex. 3/PA (0.5/1.0) | 5.4 | 6.0 | slightly cloudy after 2 mos. |
| Ex. 5 | 5.4 | 6.0 | clear |
| Ex. 5 | 5.4 | 6.5 | slightly cloudy |

[a] Weight ratios
[b] PA = Unirez 2973

Thus, according to the present invention, a solid (for example, gel or stick) composition, having enhanced compatibility with silicone fluids, is provided. The compositions can provide clear cosmetic (for example, antiperspirant and/or deodorant) compositions, utilizing a polyamide gelling agent, while providing a composition having improved application and cosmetic properties, including reduced tackiness and stickiness.

Formulations which could be used to form actual products are shown as follows. A composition of the invention may be substituted for the term "silicon-modified polyamide (gellant)".

| 1) | Deodorant stick | |
|---|---|---|
| | silicon-modified polyamide (gellant) | 12% |
| | C12–15 alkyl lactate (Ceraphyl 41) (emollient) | 35% |
| | cyclomethicone (silicone fluid) | 52% |
| | fragrance (deodorant active) | 1% |

| 2) | Antiperspirant stick | |
|---|---|---|
| | silicon-modified polyamide (gellant) | 12% |
| | aluminum chlorohydrate (antiperspirant active) | 25% |
| | cyclomethicone (silicone fluid) | 35% |
| | C12–15 alkyl lactate (Ceraphyl 41) (emollient) | 28% |
| 3) | Deodorant gel | |
| | silicon-modified polyamide (gellant) | 6% |
| | C12–15 alkyl lactate (Ceraphyl 41) (emollient) | 38% |
| | cyclomethicone (silicone fluid) | 55% |
| | fragrance (deodorant active) | 1% |

While we have shown and described several embodiments in accordance with the present invention, it is understood that the same is not limited thereto, but is susceptible to numerous changes and modifications as known to one having ordinary skill in the art, and we therefor do not wish to be limited to the details shown and described herein, but intend to cover all such modifications as are encompassed by the scope of the appended claims.

We claim:

1. A solid cosmetic composition, comprising:
   a base composition comprising a solvent and a thickening agent in an amount sufficient to provide a solid cosmetic composition wherein:
   (a) the solvent comprises a silicone fluid and is included in an amount sufficient such that the thickening agent can be dissolved therein at a temperature of 25–150 degrees C. to form a translucent or clear solution and gelled therefrom;
   (b) the thickening agent comprises a wax containing silicon moieties and a polyamide to enhance compatibility of the silicone fluid in the composition; and
   (c) the wax comprises 1–100 repeat units selected from the group consisting of dialkyl siloxane and diaryl siloxane groups wherein each alkyl is independently selected from the group consisting of methyl, ethyl, propyl and isopropyl, and each aryl is phenyl optionally substituted with 1, 2, or 3 methyl or ethyl groups.

2. A cosmetic composition according to claim 1, wherein the composition contains at least one additional silicone fluid.

3. A cosmetic composition according to claim 1, wherein the composition contains at least one active ingredient.

4. A cosmetic composition according to claim 1, wherein the active cosmetic material is a deodorant active material, whereby the composition is a deodorant composition.

5. A cosmetic composition according to claim 1, wherein the active cosmetic material is an antiperspirant active material, incorporated in the composition in an amount sufficient to reduce amount of perspiration, whereby the composition is an antiperspirant composition.

6. The antiperspirant composition according to claim 5, wherein said antiperspirant active material comprises at least one antiperspirant active aluminum salt.

7. The antiperspirant composition according to claim 6, wherein said composition is a clear composition.

8. A cosmetic composition according to claim 1, wherein said composition is a clear composition.

9. A cosmetic composition according to claim 1, wherein the thickening agent is included in the composition in an amount sufficient to form a cosmetic gel composition.

10. A cosmetic composition according to claim 1, wherein the thickening agent is included in the composition in an amount sufficient to form a cosmetic stick composition.

11. A cosmetic composition according to claim 1, wherein said thickening agent comprises a wax and a polyamide gelling agent both of which contain silicon-containing moieties.

12. A cosmetic composition according to claim 1, wherein the polyamide gelling agent is a copolymer formed from a diamino or diacid siloxane monomer.

13. A cosmetic composition according to claim 12, wherein the siloxane monomer is a siloxane diamine, the siloxane diamine reacting with a dicarboxylic acid to form the polyamide gelling agent.

14. A cosmetic composition according to claim 13, wherein the siloxane diamine has the following formula:

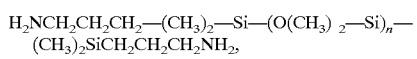

where n has a value from 1 to 300.

15. A cosmetic composition according to claim 14 wherein n has a value of 1 to 100.

16. A cosmetic composition according to claim 15 wherein n has a value of 10 to 40.

17. A cosmetic composition according to claim 16 wherein n has a value of 10 to 30.

18. A cosmetic composition according to claim 12, wherein the copolymer is the reaction product of a dimer acid, a siloxane diamine and another diamine.

19. A cosmetic composition according to claim 1, wherein the polyamide gelling agent is an agent formed by reacting free acid sites on an original polyamide with oligosiloxanes each containing at least one amine group.

20. A cosmetic composition according to claim 1, wherein the polyamide gelling agent is an agent formed by substituting an oligosiloxane diamine for a diamine, in an original polyamide formed by reacting the diamine with a dimer acid.

21. A cosmetic composition according to claim 1, wherein the polyamide gelling agent is an agent formed by grafting pendant oligosiloxane groups on an original polyamide.

22. A cosmetic composition according to claim 1, wherein said thickening agent further comprises a second polyamide gelling agent as an additional thickening agent.

23. A cosmetic composition according to claim 1, wherein the wax is (a) a siloxane diamide waxy; and (b) a reaction product of stearic acid and an alpha, omega-bis (aminopropyl) oligodimethylsiloxane.

24. A cosmetic composition according to claim 23, wherein said thickening agent comprises a polyamide gelling agent which is a reaction product of a dimer acid and a diamine.

25. A cosmetic composition according to claim 1, wherein said silicon-containing moieties are siloxane moieties.

26. A cosmetic composition according to claim 1, wherein the amide thickening agent includes a polyamide gelling agent having silicon-containing moieties, and the cosmetic composition includes, in percent by weight of the total weight of the composition, 10–95% solvent and 2–40% of said polyamide gelling agent.

27. A cosmetic composition according to claim 26, wherein the composition includes 1–95% by weight silicone fluid, of the total weight of the composition.

28. A cosmetic composition according to claim 27, wherein the silicone fluid is included in the composition in an amount of 50–95% by weight, of the total weight of the composition.

29. A cosmetic composition according to claim 1, wherein the thickening agent comprises a siloxane diamide wax and a polyamide gelling agent, the composition including, in percent by weight of the total weight of the composition, 10–95% solvent, 2–40% polyamide gelling agent, and 1–20% siloxane diamide wax.

30. A cosmetic composition according to claim 29, wherein the composition includes 1–95% by weight silicone fluid, of the total weight of the composition.

31. A cosmetic composition according to claim 30, wherein the silicone fluid is included in the composition in an amount of 50–95% by weight, of the total weight of the composition.

32. A cosmetic composition according to claim 1 wherein said cosmetic composition comprises a base composition comprising in percent by weight of the total weight of the cosmetic composition, 10–95% solvent, 2–40% polyamide gelling agent, and 1–20% siloxane diamide wax.

33. A cosmetic composition according to claim 32, wherein the base composition comprises 1–95% by weight silicone fluid, of the total weight of the cosmetic composition.

34. A cosmetic composition according to claim 33, wherein the base composition comprises 50–95% by weight silicone fluid, of the total weight of the cosmetic composition.

35. A composition according to claim 1 further comprising additional solvents selected from the group consisting of solvents which are themselves miscible in the silicon fluid and mixtures of solvents which as a mixture are miscible in the silicone fluid.

36. A method of making a solid cosmetic composition, comprising the steps of:

(a) obtaining a wax having silicon-containing moieties;

(b) obtaining a polyamide, said polyamide optionally having silicon-containing moieties;

(c) combining said wax and said polyamide to form a thickening agent which can be dissolved in a solvent comprising a silicone fluid at a temperature of 25–150 degrees C. to form a translucent or clear solution and gelled therefrom;

(d) mixing said thickening agent with a cosmetically active material, the solvent for the thickening agent, an amount of cosmetically active material sufficient to achieve a cosmetic effect, an amount of the thickening agent sufficient to provide the composition as a solid, and an amount of the solvent in the composition being sufficient to dissolve the thickening agent, so as to form a mixture; and (e) forming the mixture into a solid, so as to thereby provide the solid cosmetic composition.

37. The method according to claim 36, wherein the step of forming the polyamide includes reacting a siloxane diamine with a dimer acid as to form a polyamide gelling agent containing silicon moieties.

38. The method according to claim 37, wherein the step of forming the amide includes reacting a diamine with a dicarboxylic acid, the dicarboxylic acid containing siloxane groups.

39. The method according to claim 38, wherein the step of forming the polyamide includes reacting a polyamide having free acid terminal sites with an oligosiloxane amine or alcohol so as to incorporate silicone moieties at the terminal sites.

40. The method according to claim 38, wherein the oligosiloxane amine is selected from the group consisting oligosiloxane monoamines and diamines.

41. The method according to claim 40, wherein the oligosiloxane alcohol is selected from the group consisting of oligosiloxane monohydroxyalkyl and dihydroxyalkyl compounds.

42. The method according to claim 38, wherein the step of forming the amide includes subjecting a polyamide to a transamidation reaction to substitute oligosiloxane diamines for a diamine component of the polyamide, so as to incorporate the oligosiloxane diamines in the polyamide.

43. The method according to claim 38, wherein the step of forming the amide includes grafting pendant oligosiloxane groups on an original polyamide.

44. The method according to claim 43, wherein the original polyamide has unsaturated bonds, and the oligosiloxane groups are grafted on the original polyamide by hydrosilylation of the unsaturated bonds.

45. The method according to claim 44, wherein the oligosiloxane groups are grafted on the original polyamide by silylation of amide groups of the original polyamide.

46. The method according to claim 43, wherein the original polyamide has unsaturated bonds, and the oligosiloxane groups are grafted on the original polyamide by oxidizing the original polyamide at the unsaturated bonds and reacting the resulting product with siloxane group-containing alcohol or siloxane group-containing carboxylic acids.

47. The method according to claim 43, wherein the original polyamide has unsaturated bonds, and the oligosiloxane groups are grafted on the original polyamide by epoxidizing sites of the unsaturated bonds and reacting a resulting product of epoxidation with siloxane amines or siloxane alcohols.

48. A cosmetic composition, comprising:
  (a) an active cosmetic material, in an amount sufficient to have a cosmetically active effect;
  (b) a thickening agent comprising a wax and a polyamide gelling agent, incorporated in the composition in an amount sufficient to form a solid composition, wherein at least the wax contains silicon-containing moieties; and
  (c) a solvent for the thickening agent, in an amount sufficient such that the thickening agent can be dissolved therein at a temperature of 25°–150° C. to form a translucent or clear solution and gelled therefrom, the solvent including a silicone fluid, whereby the thickening agent including silicon-containing moieties enhances compatibility of the silicone fluid in the composition as compared to where a thickening agent without silicon-containing moieties is used.

49. A cosmetic composition, comprising:
  (a) an active cosmetic material, in an amount sufficient to have a cosmetically active effect;
  (b) a thickening agent comprising a siloxane diamide wax and a polyamide gelling agent wherein the polyamide gelling agent and siloxane diamide wax are included in the composition in an amount sufficient to form a solid composition; and
  (c) a solvent for the polyamide gelling agent and the siloxane diamide wax, the solvent including a silicone fluid, the solvent being incorporated in the composition in an amount sufficient such that the polyamide gelling agent and the siloxane diamide wax can be dissolved therein at a temperature of 25°–150° C. to form a translucent or clear solution and gelled therefrom, the siloxane diamide wax enhancing compatibility of the silicone fluid in the composition as compared to a composition containing said polyamide gelling agent and no siloxane diamide wax.

* * * * *